(12) United States Patent
Luster

(10) Patent No.: US 10,631,793 B1
(45) Date of Patent: Apr. 28, 2020

(54) IMPACT INDICATOR

(71) Applicant: Eric Levell Luster, Laveen, AZ (US)

(72) Inventor: Eric Levell Luster, Laveen, AZ (US)

( * ) Notice: Subject to any disclaimer, the term of this patent is extended or adjusted under 35 U.S.C. 154(b) by 376 days.

(21) Appl. No.: 14/999,232

(22) Filed: Apr. 13, 2016

Related U.S. Application Data

(60) Provisional application No. 62/178,639, filed on Apr. 14, 2015.

(51) Int. Cl.
| | |
|---|---|
| *A61B 5/00* | (2006.01) |
| *A63B 71/06* | (2006.01) |
| *A41D 20/00* | (2006.01) |
| *A61B 5/11* | (2006.01) |

(52) U.S. Cl.
CPC ............ *A61B 5/7275* (2013.01); *A41D 20/00* (2013.01); *A61B 5/0004* (2013.01); *A61B 5/1121* (2013.01); *A61B 5/6823* (2013.01); *A61B 5/6824* (2013.01); *A61B 5/6828* (2013.01); *A61B 5/6829* (2013.01); *A61B 5/6831* (2013.01); *A61B 5/742* (2013.01); *A61B 5/7405* (2013.01); *A61B 5/746* (2013.01); *A63B 71/06* (2013.01); *A61B 2503/06* (2013.01); *A61B 2503/10* (2013.01); *A61B 2562/0219* (2013.01)

(58) Field of Classification Search
CPC ... A61B 5/7275; A61B 5/6823; A61B 5/7405; A61B 5/742; A61B 5/0004; A61B 5/6831; A61B 5/746; A61B 5/6824; A61B 5/6828; A61B 5/6829; A61B 5/1121; A61B 2562/0219; A61B 2503/06; A61B 5/11; A61B 5/6803; A61B 2503/10; A61B 5/0022; A61B 5/6895; A61B 2017/00075; A41D 20/00; A63B 71/06

USPC .......... 600/300, 587, 595, 549, 301; 702/41, 702/141
See application file for complete search history.

(56) References Cited

U.S. PATENT DOCUMENTS

| | | | | |
|---|---|---|---|---|
| 6,854,133 | B2 * | 2/2005 | Lee ........................ | A42B 3/063 2/412 |
| 7,383,728 | B2 * | 6/2008 | Noble .................. | A61B 5/1116 600/595 |
| 8,556,831 | B1 * | 10/2013 | Faber .................... | A42B 3/046 340/500 |

(Continued)

*Primary Examiner* — May A Abouelela
(74) *Attorney, Agent, or Firm* — Schmeiser, Olsen & Watts LLP

(57) ABSTRACT

Method for warning a coach in real-time that a team player suffered head injuries why playing on a sports field with other players present, comprising the steps of:
  having the player wear a headband with one battery powered multi-axial motion sensor mounted on the rear;
  measuring with the sensor 3-D (X-Y-Z) accelerations out of which 2-D (X-Y) is in essentially horizontal plane when the player is standing facing forward; establishing head bank, roll and yaw angular acceleration thresholds for mild, moderate and severe head injuries; having an applet calculate the angular accelerations form the linear accelerations or measure angular accelerations directly; comparing measured angular accelerations to threshold angular accelerations; warn the coach about the occurrence of threshold exceedances indicating mild, moderate or severe head injuries; log the time of the threshold exceedances along with the measured values of the angular accelerations. Said warning are yellow, orange or red colors or low, moderate and high frequency beeps or both.

7 Claims, 7 Drawing Sheets

(56) References Cited

U.S. PATENT DOCUMENTS

| | | | | |
|---|---|---|---|---|
| 8,797,165 B2* | 8/2014 | Greenwald | A61B 5/0002 | 340/573.1 |
| 8,842,841 B2* | 9/2014 | Hook | H04L 9/14 | 380/277 |
| 9,075,405 B1* | 7/2015 | Anvari | G05B 13/02 | |
| 2002/0060633 A1* | 5/2002 | Crisco, III | A42B 3/046 | 340/669 |
| 2002/0087101 A1* | 7/2002 | Barrick | A61B 5/1077 | 600/587 |
| 2005/0177929 A1* | 8/2005 | Greenwald | A42B 3/046 | 2/425 |
| 2006/0074338 A1* | 4/2006 | Greenwald | A61B 5/0002 | 600/549 |
| 2011/0219852 A1* | 9/2011 | Kasten | A61B 5/11 | 73/12.04 |
| 2012/0219852 A1* | 8/2012 | Huang | H01M 4/13 | 429/199 |
| 2013/0060168 A1* | 3/2013 | Chu | A42B 3/046 | 600/595 |
| 2013/0110415 A1* | 5/2013 | Davis | A42B 3/046 | 702/41 |
| 2013/0303946 A1* | 11/2013 | Gettens | A61B 5/11 | 600/587 |
| 2014/0052405 A1* | 2/2014 | Wackym | G01P 15/00 | 702/141 |
| 2014/0081180 A1* | 3/2014 | Ghajar | A61F 5/055 | 600/595 |
| 2014/0081601 A1* | 3/2014 | Zhang | A42C 2/00 | 703/1 |
| 2014/0149067 A1* | 5/2014 | Merril | A61B 5/11 | 702/141 |
| 2014/0247129 A1* | 9/2014 | de la Fuente | A42B 3/046 | 340/573.1 |
| 2014/0364772 A1* | 12/2014 | Howard | A42B 3/046 | 600/595 |
| 2015/0040685 A1* | 2/2015 | Nicholson | A61B 5/4064 | 73/862.51 |
| 2015/0173666 A1* | 6/2015 | Smith | A61B 5/11 | 600/301 |

\* cited by examiner

IMPACT INDICATOR

CROSS-REFERENCE TO RELATED APPLICATION

This application claims the benefit of United States Provisional Patent Application Ser. No. 62/178,639, filed on Apr. 14, 2015, and titled "IMPACT INDICATOR", filed by inventors Eric Luster and Adolph Seema.

FIELD OF THE INVENTION

This invention relates body part impact indicators. More specifically to wearable acceleration sensors signaling danger level of concussion using a special headband.

BACKGROUND OF THE INVENTION

The invention addresses the need for a headband with built in accelerometer and transducer aimed to warn parents on the sidelines watching their children playing on the field and wanting to know if an apparently innocent head impact raises the level of concern relating to concussion.

It is difficult to detect a mild concussion, which can become serious as time goes by. Children, young athletes and sportsmen may not notice small impacts or ignore them for wanting to keep playing. Yet it would be to their advantage to know the details of such accident. Coaches or parents may interfere accordingly or just monitor impacts for short and long term health management.

Science proved the straightforward relationship between the level of concussion and the level of impact on the head. Also that a mild or moderate concussion or head injury may have serious mental or health consequences, which may surface only years from the accident (headaches, blurry vision, tinnitus, seizure). 70-75 g (boxer hit) impacts cause such trauma invariably. However 1-10 g impacts, if causes brain rotation, can also be critical. For instance, angular accelerations of 4600, 5900 and 7900 rad/s^2 increase the risk of concussion by 25, 50 and 80% respectively. Higher than 20,000 rad/s^2 has not been measured even in boxing.

Modern technology shrunk the size and cost of battery operated accelerometer-transducer-transmitter packages. That makes it possible to build such device in the pouch of wearables like headband, wristbands and belts.

It is desirable that such a device warns the user by sound and light to stop playing and check for latent injury. Also, that coach and parent can receive real time signals of the incident as it is happening, so they can interfere if necessary or let it go and check on it later.

Such a device is a great service to players, parents and coaches by boosting confidence level of playing field games.

It is therefore the object of the invention is to provide for such a device. Also to manage its data custodian through encrypted app and to use circular memory buffering for not to miss an event of interest. The app must prevent unauthorized data erasure of moderate threshold events. For instance, cloud stored acceleration time history erasure of serious events may be allowed by court order only.

SUMMARY OF THE INVENTION

The above problems and others are at least partially solved and the above objects and others realized in a process, which according to the teachings of this invention, uses an autonomous battery operated, fingertip size, accelerometer-transducer-transmitter (electronics) package (drop meter) hidden in the inner pouch of a headband, which is capable of the following functions:

a) Detecting impact acceleration levels on microchip level in 3 directions (X, Y and Z) at least by one transducer;
b) Transducing acceleration signals to electronic signals;
c) Transmitting signals of measured impact levels to a mobile telecommunication device (cellphone, laptop, Wi Fi cellular transmitter, Chromecast or Chromebit alike, and digital devices sensing and managing Bluetooth, Wi-Fi and Cellular broadcast);
d) Analyzing the level of impact;
e) Logging impact peak magnitude and time of occurrence;
f) Giving commands to sound beeper and LED light built into the package;
g) Assisting by computation in displaying levels of concerns on the mobile device using an app;
h) Securing data ownership, custodian and management by encryption;
i) Employing circular RAM buffering for not to miss any threshold events; and
j) Employing butterfly design for electronic components special separation and heat management, using conductive thread interconnect busses and temper proof enclosures.

The electronics may be generic or customized and may preferably use rechargeable battery, preferably to be recharged via Micro-USB connection. At least one of such electronics is to be used in said pouch in frontal position. However, two in 90° apart, 45° off from center or at 3"-4" apart, is preferable to avoid being hit and pressed in the temple. To measure rotational acceleration, two such well separated accelerometers are needed. If only one is used, the programming must assume the size of the head (7" average diameter, if unknown).

To accommodate various head sizes, the headband shall preferably made from open strip with hook-and-loop (Velcro) end connection.

The applet must calculate and display the level of concussion risk, for instant in terms of "Serious, Moderate and Mild". It however my display the g-forces as well, including their time history by a plot and the peak level accelerations and the time of occurrences by labeled numbers.

Tennis players use electronics in their racket to gauge impact forces and read the measurements and the related statistics on their cellphone. Such system can easily modified to suit the need s of the invention, thus are considered prior art and not disclosed in details.

While boxing would be the most obvious use of a headband with accelerometers in the rear, with youth, collegian, and professional in mind, the headband of this invention is rather proposed for football, baseball, hockey, basketball, soccer, running, snowboarding, skiing, ice luge, cricket, rocket ball and rugby.

Limb bands, including wrist, knee, ankle and belly (waist) are obvious extension and configuration of the headband and considered within scope without illustrations.

Said butterfly design includes the following configurations:

i. Single device, single app mode
ii. Multiple devices, single app mode
iii. Multiple devices, multiple app mode
iv. Team setup mode.

BRIEF DESCRIPTION OF THE DRAWINGS

Referring to the drawings:

FIG. 2 is a frontal view of the flattened stripe the headband of FIG. 1 is made of.

DETAILED DESCRIPTION OF A PREFERRED EMBODIMENT

Figure 1:
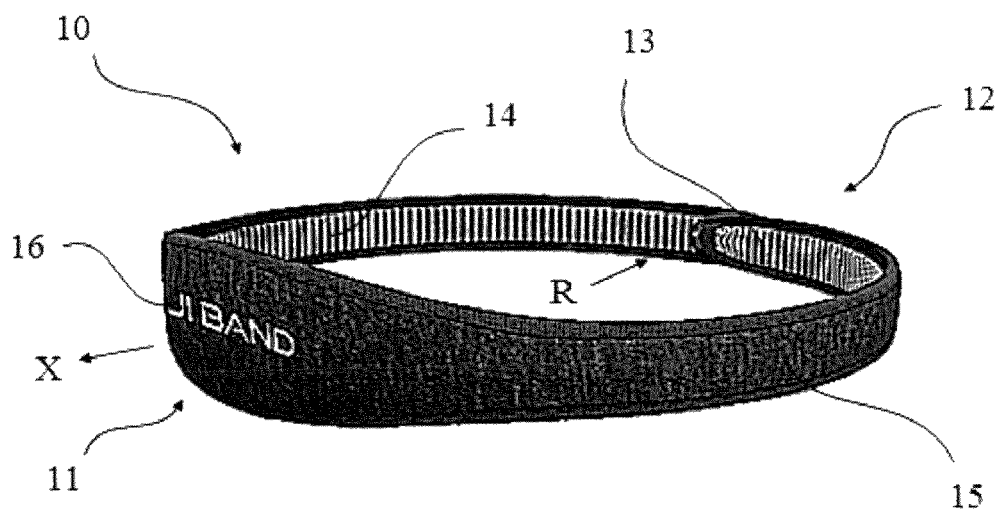
FIG. 1 is a perspective view of a headband as per the teachings of the invention.

Attention is now turned to FIG. 1, which illustrates, in perspective view, headband 10 as per the teachings of the invention.

Headband 10 has front part 11, rear part 12, hook-and-loop closure 13, inner lining mesh 14, outer lining textile 15, and logo 16 (HIJI BAND). X is the direction of the frontal acceleration and R is the average inside radius.

Figure 3:
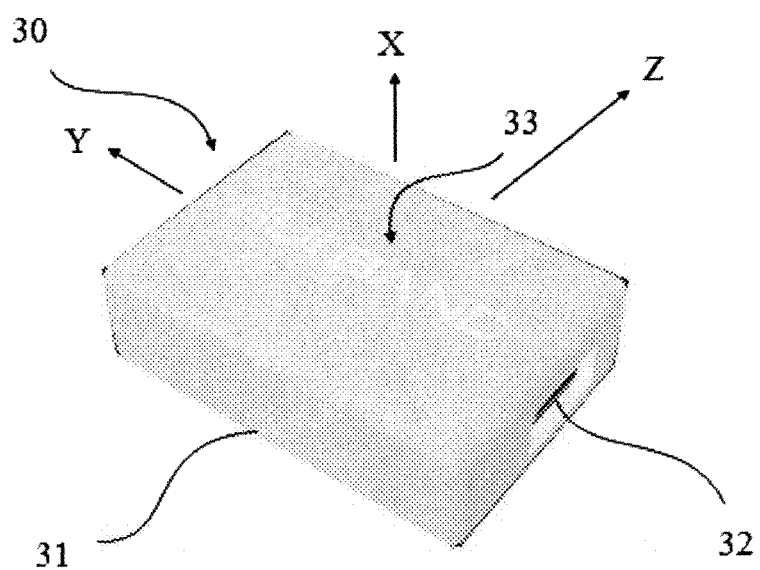
FIG. 3 is a perspective view of the electronics to be hidden in the pouch of the headband of FIG. 1.

Behind part 16, mesh 14 is split, forming a pouch (see in FIG. 5) to accommodate accelerometer electronics (see FIG. 3). Headband 10 is a machine washable garment. Next, it is shown in its stretched form.

Figure 2:
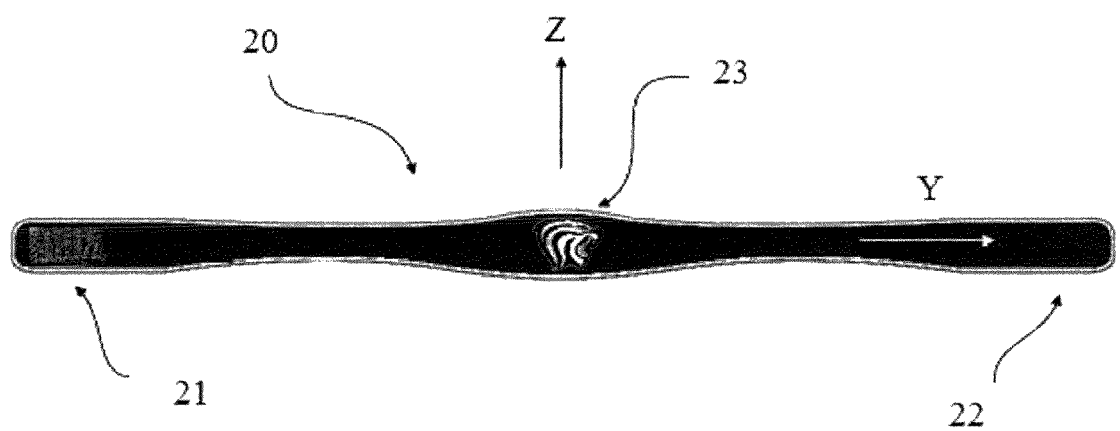

Attention is now turned to FIG. 2, which, in frontal view, illustrates flattened headband stripe 20, which is the stretched out embodiment of headband 10. Z is the vertical axis and Y is the deviatory axis.

Stripe 20 has mascot stamp 23 (catlike wild animal head), hook bed 21, and loop bed 22. Beds 21 and 22 form a hook-and-loop lock (Velcro). This however may be substituted with other customary locking devices, such as push buttons or clips. The center part of strip 20 is the frontal part of headband 10, which goes to the temple on the head. That is the best place to measure acceleration to assess concussion. The measurement device is shown next.

Attention is now turned to FIG. 3, which illustrates in perspective view, electronics 30 to be hidden in the pouch of the headband 10.

Electronics 30 includes housing 31, recharging (USB, Micro-USB, lighting or mini-sub) socket 32, and logo 33. It logs acceleration in X, Y and Z directions, identifies peak amplitudes of impacts, compare that to threshold levels, logs their time arrival, transduce acceleration and time signals, transmits these as Lime histories wirelessly.

Electronics 30 inserted into the frontal pouch of headband 10 would measure the frontal acceleration shocks, aX, in direction X, the deviatory acceleration shocks, aY in direction Y, and the vertical acceleration shocks, aZ in direction Z. The torque around the ear-to-ear head axis is obtained as aZ·R and around the vertical cranial axis as aY·R. These can be triangulated however by two electronics 30 separated in two pouches at front 11. Since R varies from person to person, though not much, the triangulation yields to more precise data, thus used in sponsored sports by coaches. Torque accelerations are directly proportional to angular accelerations, which are the real concerns of concussions, for being more critical than the linear (X, Y and Z) accelerations here, which are measured in the near zero to 200 g range, where 1 g=32.2 ft/s^2.

Electronics, suitable to configure as electronics 30 are used in tennis to measure tennis racket acceleration peaks due to tennis ball impacts. The inner workings of electronics 30 is not detailed thereof, except as illustrated in FIG. 7-10. The transmitted data of electronics 30 is processed by the applet and displayed by at least one cellphone or smartphone. That is shown next.

Figure 4:
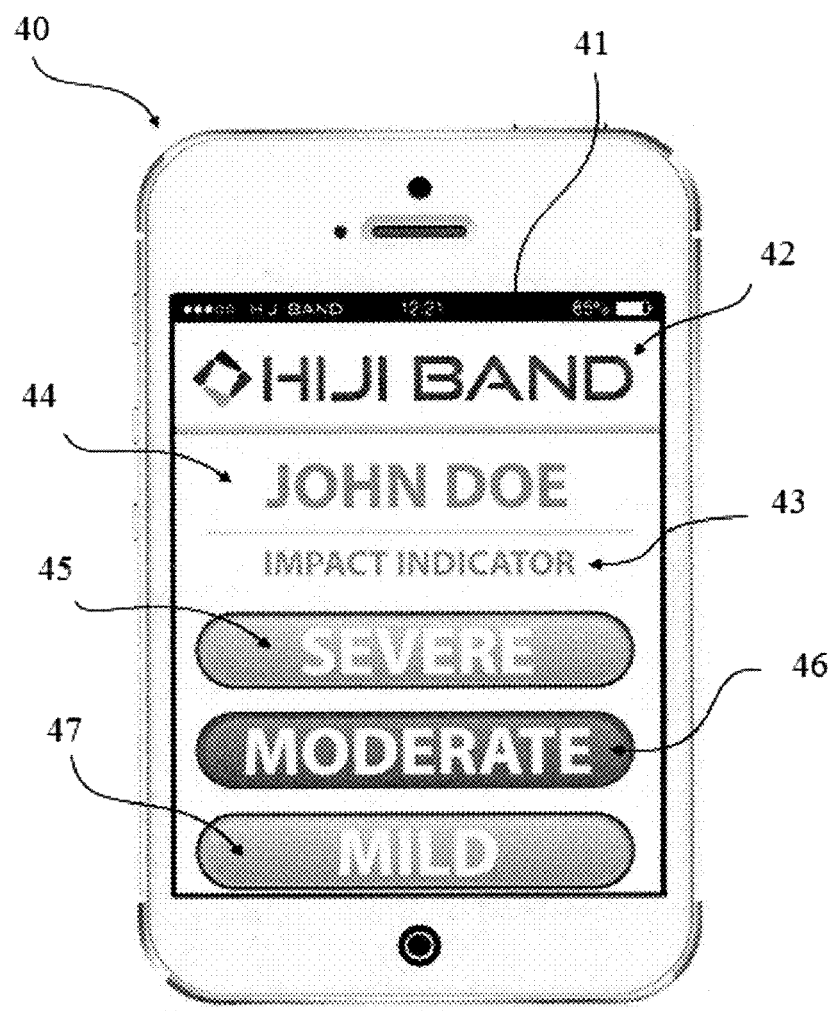
FIG. 4 is a frontal view of a cellphone displaying measured concussion risk level.

Attention is now turned to FIG. 4, which illustrates the face view (display view) of cellphone 40, which warns of concussion danger.

Cellphone 40 has display 41, which displays logo 42 (HIJI BAND), user (player) name 44 (JOHN DOE), mode of operation 43 (IMPACT INDICATOR), severe impact level 45 (SEVERE), moderate impact level 46 (MODERATE), and mild impact level 47 (MILD). When level indicator 45 is lit or blinking or turns red, the cellphone holder parent or coach may call the player out of the field to check on his condition. Concurrently with indicator 45 activation, electronics 30 lit LED pointed to direction Z and turns on beeping or a short siren warning sign, to warn the player about the high head impact occurrence, which, in the heat of the game may easily be overlooked.

Other indicators are also within the scope of the invention, for instance the displaying of the actual g-force peaks, plots and statistics about that, as well as time histories of stored acceleration data. Some researcher cares more about velocity and displacement than acceleration peaks. Since velocity is the first integral of acceleration and displacement is the integral of velocity, such data can also be processed and displayed by the applet preprogrammed into cellphone 40.

The applet processing the tennis electronics can be reconfigured to process data for concussion warning, thus not detailed here. There are other similar purpose electronics and applets, which are also suitable for being adopted and modified for the functions electronics 30 and cellphone 40 requires.

Figure 5:
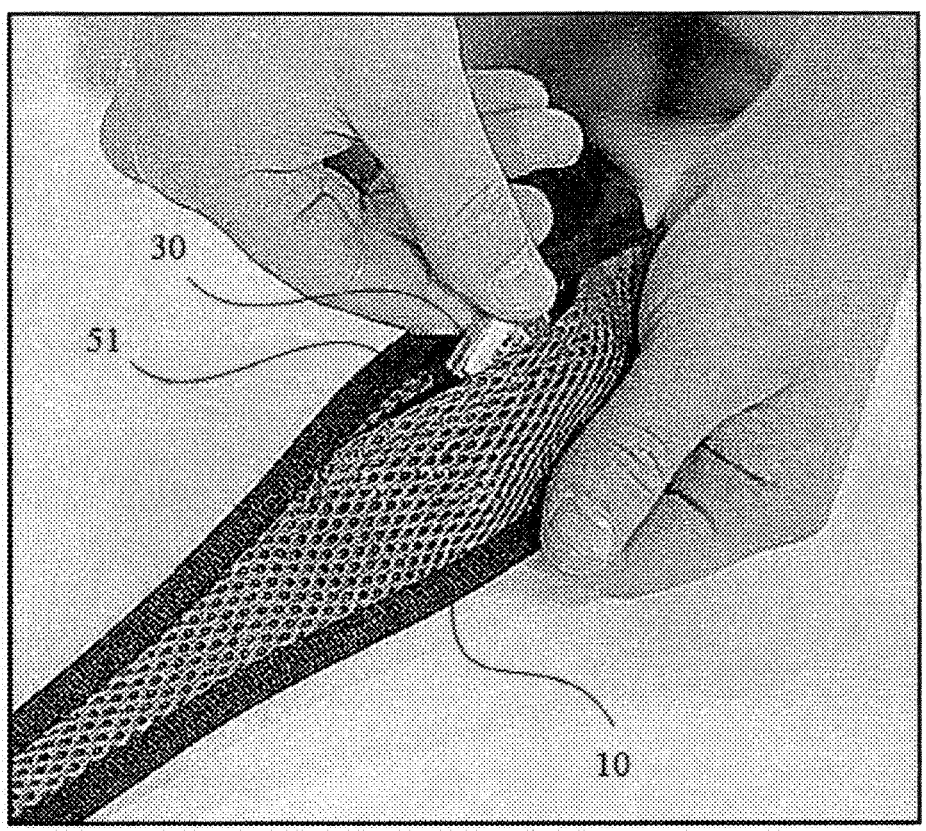
FIG. 5 is a photographic view of the process of placing the electronics into the pouch as per the teachings of the invention.

Attention is now turned to FIG. 5, which illustrates in perspective view 50 of the process of placing electronics 30 into pouch 51 of headband 10 as per the teachings of the invention.

Figure 6:
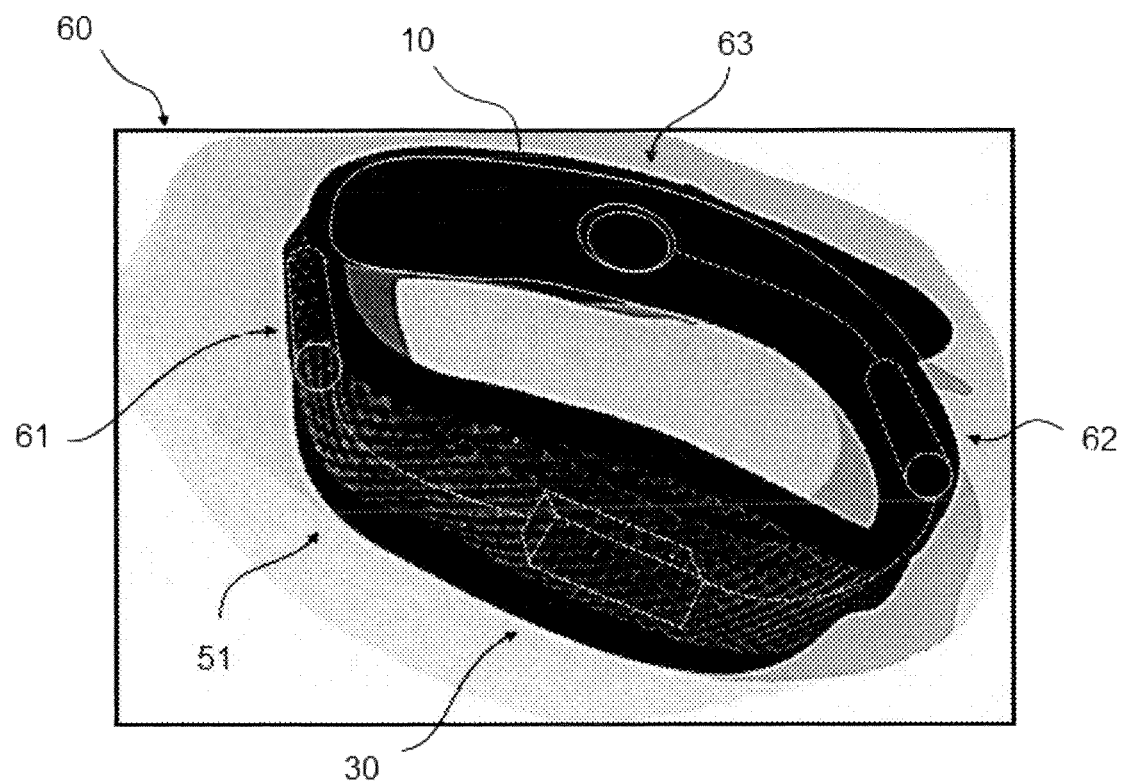
FIG. 6 is a photographic view of an exemplary headband with butterfly design componentry.

Attention is now turned to FIG. 6, which illustrates in perspective view with assembly 60 an exemplary headband turned inside out, with butterfly design componentry arrangement on actual device.

Assembly 60 has headband 10, controller-collector (CC) electronics 30, left side satellite electronic device 61, right side satellite electronic device 62, rear satellite electronic device 63, all three tethered by bus wiring to CC 30, and conductive thread wire mesh pouch 51.

Components 61-63 may be accelerometers or LEDs or buzzers or other measuring or warning devices in various configurations, some of which are illustrated next.

Figure 7:
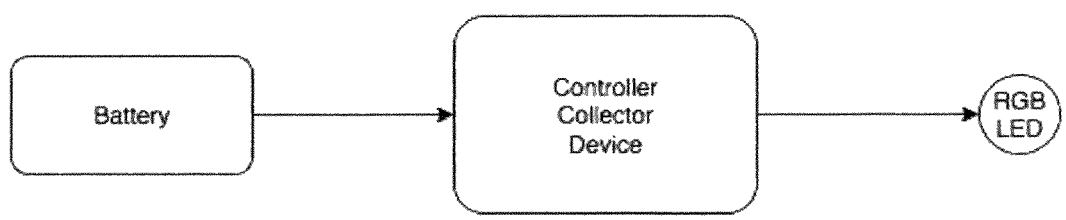
FIG. 7 is an exemplary system configuration diagram of the butterfly design.

Attention is now turned to FIG. 7, which illustrates in an exemplary system build diagram the componentry butterfly design as per the teachings of the invention.

This is the simplest system configuration, illustrating single device, single application mode of operation, with the battery and the LED indicator tethered to the CC device.

Figure 8:
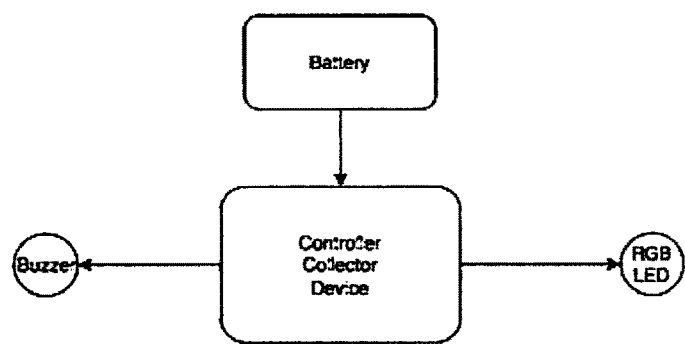
FIG. 8 is another exemplary system configuration diagram of the butterfly design.

Similarly, FIG. 8 illustrates the same, with added tethered buzzer. This is a multiple device, single app mode of operation example.

Figure 9:
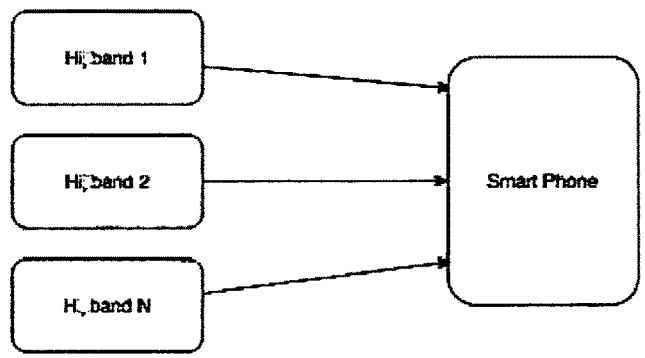
FIG. 9 is yet another exemplary system configuration diagram of the butterfly design.
Figure 10:
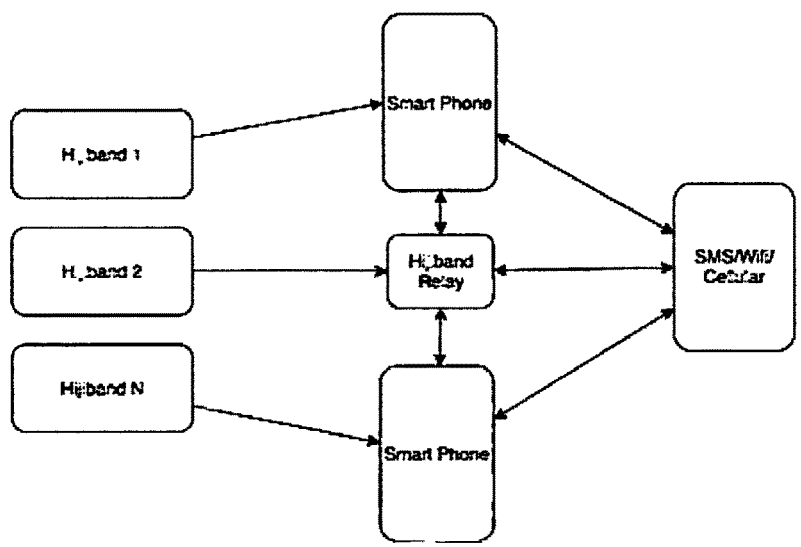
FIG. 10 is yet another exemplary system configuration diagram of the butterfly design.
Figure 11:
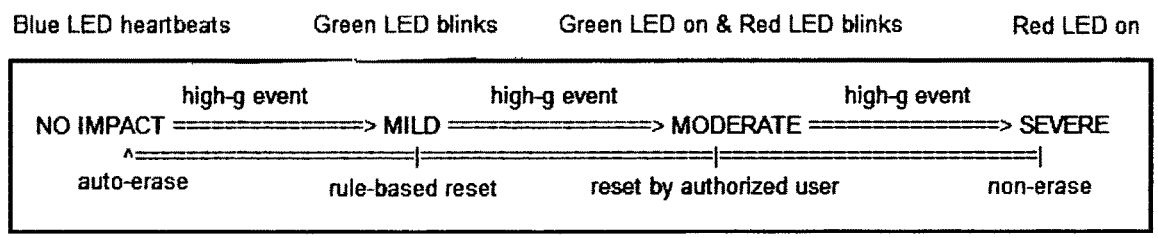
FIG. 11 is a functional diagram illustrating the threshold level acceleration triggering actions.

Furthermore, FIG. 9 illustrates a simple team setup mode and FIG. 10 a complex mode of the same.

Attention is finally turned to FIG. 10, which in a functional diagram, illustrates the threshold level acceleration triggering actions of the circular buffering RAM.

The authorization levels of erasure permits and the LED indicator modes are tied to the four levels of impact accelerations labeled NO IMPACT, MILD, MODERATE and SEVERE. The warnings are exemplified by LED actions, which however are combined with buzzer actions (not detailed for simplicity).

To the skilled in the art, it shall be obvious that headband 10 may be wrapped around the ankle or knee or elbow or wrist of a player, so a coach can use the measurements of electronics 30 for training purposes. One can also imagine extending strip 20 much longer to wrap around the belly. Elongating pouch 51 and placing two electronics 30 in double compartments, shall also be obvious without further illustration.

The present invention is described above with reference to a preferred embodiment. However, those skilled in the art will recognize that changes and modifications may be made in the described embodiment without departing from the nature and scope of the present invention. For instance, replacing cellphone with other mobile computing device, such as tablet or laptop is considered intuitive and thereby within the scope of this invention.

Various further changes and modifications to the embodiment herein chosen for purposes of illustration will readily occur to those skilled in the art. To the extent that such modifications and variations do not depart from the spirit of the invention, they are intended to be included within the scope thereof.

Having fully described the invention in such clear and concise terms as to enable those skilled in the art to understand and practice the same, the invention claimed is:

1. A method of using a head injury alert device by a player comprising
   wearing a headband by the player, wherein the headband is configured to be worn alone by the player, and wherein the headband comprises two controller-collectors, each of the two controller-collectors having an accelerometer, a transducer and a transmitter;
   two conductive wire thread mesh inner pouches in a frontal portion of the headband, the two controller-collectors positioned in a separate pouch of the two conductive wire thread mesh inner pouches;
   a left side component;
   a right side component; and
   a rear component, wherein the left side component, the right side component and the rear component are tethered by bus wiring to the two controller-collectors;
   detecting impact acceleration levels in three directions by each of the transducers;
   transducing acceleration signals to electronic signals; and
   transmitting the electronic signals of the impact acceleration levels to a mobile device,
   wherein torque around an ear to ear head axis and around a vertical cranial axis is triangulated by the two controller-collectors.

2. The method of claim 1, wherein the left side component, the right side component and the rear component are measuring or warning devices selected from the group consisting of an acceleration sensor, a beeper, a buzzer and/or an LED light.

3. The method of claim 2, wherein each of the two controller-collectors activates the beeper, buzzer and/or light when the impact acceleration levels meet a predetermined threshold.

4. The method of claim 1, wherein each of the two controller-collectors activates a display on the mobile device when the impact acceleration levels meet a predetermined threshold.

5. The method of claim 1, wherein each of the two controller-collectors measures frontal acceleration shocks, deviatory acceleration shocks and vertical acceleration shocks.

6. The method of claim 1, wherein the mobile device is used by a coach of a team, and wherein the mobile device receives the electronic signals of the impact acceleration levels from each of the players on the team.

7. The method of claim 1, wherein the two controller-collectors are positioned about 3 to about 4 inches apart.

* * * * *

UNITED STATES PATENT AND TRADEMARK OFFICE
CERTIFICATE OF CORRECTION

| | | |
|---|---|---|
| PATENT NO. | : 10,631,793 B1 | Page 1 of 1 |
| APPLICATION NO. | : 14/999232 | |
| DATED | : April 28, 2020 | |
| INVENTOR(S) | : Eric Levell Luster and Adolph Seema | |

It is certified that error appears in the above-identified patent and that said Letters Patent is hereby corrected as shown below:

On the Title Page

Item (72) Inventors should read:
Eric Levell Luster
Adolph Seema

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*